(12) United States Patent
Yoshida et al.

(10) Patent No.: US 9,429,541 B2
(45) Date of Patent: Aug. 30, 2016

(54) GAS SENSOR ELEMENT, GAS SENSOR AND CONTROL SYSTEM OF GAS SENSOR

(75) Inventors: Shin Yoshida, Aichi (JP); Shigeki Mori, Seki (JP); Takeshi Kawai, Komaki (JP); Hiroshi Inagaki, Komaki (JP); Seiji Oya, Aichi (JP); Kentaro Mori, Inuyama (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 365 days.

(21) Appl. No.: 13/037,982

(22) Filed: Mar. 1, 2011

(65) Prior Publication Data

US 2011/0214988 A1 Sep. 8, 2011

(30) Foreign Application Priority Data

Mar. 2, 2010 (JP) .................................. 2010-045899

(51) Int. Cl.
G01N 27/417 (2006.01)

(52) U.S. Cl.
CPC .................................. G01N 27/417 (2013.01)

(58) Field of Classification Search
CPC .................................................. G01N 27/417
USPC .................................................. 204/424, 421
See application file for complete search history.

(56) References Cited

U.S. PATENT DOCUMENTS

| | | | |
|---|---|---|---|
| 3,843,400 A * | 10/1974 | Radford | 429/152 |
| 5,236,569 A * | 8/1993 | Murase et al. | 204/412 |
| 5,844,122 A * | 12/1998 | Kato | 73/1.06 |
| 6,635,161 B2 * | 10/2003 | Inagaki | 204/425 |
| 8,330,470 B2 | 12/2012 | Bevot et al. | |
| 2006/0091007 A1 * | 5/2006 | Inoue et al. | 204/406 |
| 2009/0217737 A1 * | 9/2009 | Dorfmueller et al. | 73/28.01 |

FOREIGN PATENT DOCUMENTS

| | | |
|---|---|---|
| DE | 10 2008 011231 A1 | 5/2009 |
| EP | 0 973 029 A1 | 1/2000 |
| JP | 9-015201 A | 1/1997 |
| JP | 2003-185626 A | 7/2003 |

OTHER PUBLICATIONS

German Office Action in corresponding German application No. DE 10 2011 001 028.9, dated May 24, 2013.

* cited by examiner

*Primary Examiner* — Luan Van
*Assistant Examiner* — Louis Rufo
(74) *Attorney, Agent, or Firm* — Sughrue Mion, PLLC

(57) ABSTRACT

In order to compensate for variation in output of sensor elements 10, there is provided a compensating resistor 220 that has a resistance value reflected by correction information. The resistor 220 is connected in parallel with a VS cell 245 through paired electrode leads 236 and 237 and paired electrode pads 232 and 233. The paired electrode leads 236 and 237 are placed at a position electrically isolated from solid electrolyte substrates 120 and 140.

8 Claims, 6 Drawing Sheets

GAS SENSOR ELEMENT, GAS SENSOR AND CONTROL SYSTEM OF GAS SENSOR

BACKGROUND OF THE INVENTION

1. Field of the Invention

The present invention relates to a gas sensor element and a gas sensor for detecting the concentration of a specific gas in gaseous environment, and a control system of the gas sensor.

2. Description of the Related Art

Hitherto, for detecting the concentration of oxygen in the exhaust gas from an internal combustion engine of a motor vehicle, various types of gas (viz., oxygen) sensors have been proposed and put into practical use. Some of them are of a type that uses a gas sensor element which comprises a cell including a solid electrolyte body of zirconia or the like and a pair of electrodes having the solid electrolyte body intimately put therebetween. The concentration of a specified gas is detected based on current flowing between the electrodes through the solid electrolyte body.

As is known, the gas sensor elements are those that tend to show variations in output caused by variations in production. For compensating the variations in the output of sensor elements, various measures have been proposed, one of which is shown in Japanese Laid-open Patent Application (Tokkaihei) 9-15201.

In the measures shown in the publication, there are provided a resistor that is provided on a surface of a ceramic substrate to serve as a detecting section and a voltage-dividing resistor (or compensating resistor) that is connected to the detecting resistor in parallel. By applying a LASER trimming to the voltage-dividing resistor, the value of the resistance (or resistance value) is adjusted. With such measures, a plurality of sensor elements produced are able to exhibit even outputs.

SUMMARY OF THE INVENTION

Due to inherent construction of the sensor element of the publication, temperature changes of the ceramic substrate per se do not bring about substantial changes in resistance value of the same. Thus, in such sensor element, adjustment of output is easily achieved by connecting the voltage-dividing resistor to the detecting resistor in parallel.

However, if the above-mentioned measures are simply applied to a gas sensor element that comprises a cell including a solid electrolyte body and a pair of electrodes having the solid electrolyte body put therebetween, temperature changes of the solid electrolyte body bring about considerable changes in resistance value of the same. Thus, in this case, the contribution degree of the compensating resistor to the output adjustment of the sensor element is varied depending on the temperature to which the solid electrolyte body is exposed, and thus, adjustment of output of the sensor element has to be made by paying attention to the temperature change of the solid electrolyte body. In short, in this case, provision of the compensating resistor has to be made by paying attention of the temperature change of the solid electrolyte body, which inevitably causes a complicated construction of the sensor element.

It is therefore an object of the present invention to provide a gas sensor element which is free of the above-mentioned drawbacks.

More specifically, it is an object of the present invention to provide an economical gas sensor element which comprise a cell including a solid electrolyte body and a pair of electrodes having the solid electrolyte body put therebetween and is able to accurately compensate the output of the gas sensor element.

It is another object of the present invention to provide a gas sensor and a control system of the gas sensor, to which the gas sensor element is practically applied.

In accordance with a first embodiment of the present invention, there is provided a gas sensor element which has at least one cell that includes a solid electrolyte substrate and a pair of electrodes having the solid electrolyte substrate intimately put therebetween, so that the gas sensor element outputs an information signal representative of a concentration of a specified gas in a gaseous environment, in which the cell is of a type in which, for outputting the information signal, current is forced to flow through one of the paired electrodes, the solid electrolyte substrate and the other of the paired electrodes, a compensating resistor is integrally provided by the gas sensor element, the compensating resistor having a resistance value reflected by a correction information used for correcting the information signal, and the compensating resistor is connected in parallel with the cell through a pair of current flow lines and placed at a position electrically isolated from the solid electrolyte substrate.

In the first embodiment of the invention, the compensating resistor is connected to the cell in parallel manner, and thus, a work for getting the resistance value of the compensating resistor and a work for directing current to the cell are achieved by using common current flow lines. That is, there is no need of providing current flow lines for each work, which brings about reduction in cost. The current flow lines to the compensating resistor are electrically isolated from the solid electrolyte substrates. Thus, even when the resistance value of the solid electrolyte substrate is considerably changed due to a temperature change, information on the resistance value of the compensating resistor is obtainable without being affected by the resistance change of the solid electrolyte substrate. Accordingly, by using a corrected information calculated based on information obtained from the gas sensor element without being affected by the change of the resistance value of the solid electrolyte substrate, information signal issued from the gas sensor element can be corrected. That is, it is possible to obtain a detected signal that is precisely corrected in variation of production of the gas sensor elements.

Getting of information on the resistance value of the compensating resistor should be made preferably before the activation of the solid electrolyte substrate. That is, such getting should be made under a condition of room temperature. Under inactivated condition, the solid electrolyte substrate fails to show an oxygen ion conductivity, which means that it has a high resistance value. Thus, if getting of the resistance value of the compensating resistor is made under the inactivated condition of the solid electrolyte substrate, information on change of the resistance value of the compensating resistor is precisely obtained without being affected by the resistance value of the solid electrolyte substrate.

In the first embodiment, the resistance value of the compensating resistor may be lower than a resistance value which is shown by the solid electrolyte substrate under a condition of room temperature, and may be a value which is more than ten times as much as a resistance value which is shown by the solid electrolyte substrate under a condition of temperature of 800° C. With these features, if the cell and the compensating resistor are subjected to voltage application under a condition of room temperature, only the compensating resistor permits current flow therethrough because the solid electrolyte substrate shows a high resistance (viz., non-conductivity) against current flow under such room temperature condition, and thus, information on the resistance value of the compensating resistor is precisely obtained. Furthermore, if the cell and the compensating resister are subjected to voltage application under a condition of 800° C., only the solid electrolyte substitute permits current flow therethrough because the compensating resistor shows a very high resistance value as compared with the solid electrolyte substrate under such high temperature condition, and thus, the cell can be fed with a desired amount of current without being affected by the compensating resistor. Under such high temperature condition, the resistance value of the cell is quite small as compared with that of the compensating resistor, and thus, the compensating resistor connected in parallel with the cell makes substantially no influence on operation of the cell.

In the first embodiment, the cell may be an oxygen generating cell that generates oxygen when a constant current is forced to flow through the cell. In this case, due to flowing of the constant current through the oxygen generating cell, the resistance value of the compensating resistor is easily obtained by forcing the constant current to flow through the compensating resistor.

In the first embodiment, the compensating resistor may be covered with a protecting layer to protect the compensating resistor from surrounding gas. Due to provision of the such protecting layer, undesired contact between the compensating resistor and the surrounding gas is completely blocked. With such protecting layer, the compensating resistor is protected from being affected by the temperature of the gas, which improves the effect of detecting the resistance value of the compensating resistor.

In the first embodiment, the compensating resistor may be trimmed to have an adjustable resistance value that is reflected by the correction information. Usage of trimming for adjusting the resistance value of the compensating resistor brings about easiness with which fine adjustment of the resistance value is carried out.

In a second embodiment of the present invention, there is provided a gas sensor that comprises the gas sensor element of the first embodiment and a housing that holds therein the gas sensor element. When such gas sensor is used for detecting a concentration of specified gas in a gaseous environment, it is possible to obtain information signal that is precisely compensated from variations of production of the gas sensor element.

In a third embodiment of the present invention, there is provided a gas sensor control system which comprises a gas sensor of the second embodiment, and a control unit electrically connected to the gas sensor and provided in a place apart form the gas sensor, wherein the control unit comprises a first processing means that provides a first information signal representative of a resistance value of the compensating resistor; a second processing means that provides a second information signal representative of the concentration of the specified gas; and a third processing means that calculates the correction information in accordance with the first information signal and corrects the second information signal in accordance with the calculated correction information. When this type of control system is practically used, it is possible to obtain information signal that is precisely compensated from variations of production of the gas sensor element.

BRIEF DESCRIPTION OF THE DRAWINGS

Other objects and advantages of the present invention will become apparent from the following description when taken in conjunction with the accompanying drawings, in which.

DETAILED DESCRIPTION OF THE INVENTION

In the following, the present invention will be described in detail with reference to the accompanying drawings.

Referring to FIGS. 1 to 4, there is shown a gas sensor 1 according to the present invention. Actually, the gas sensor 1 shown is of a type that senses oxygen concentration.

Figure 1:
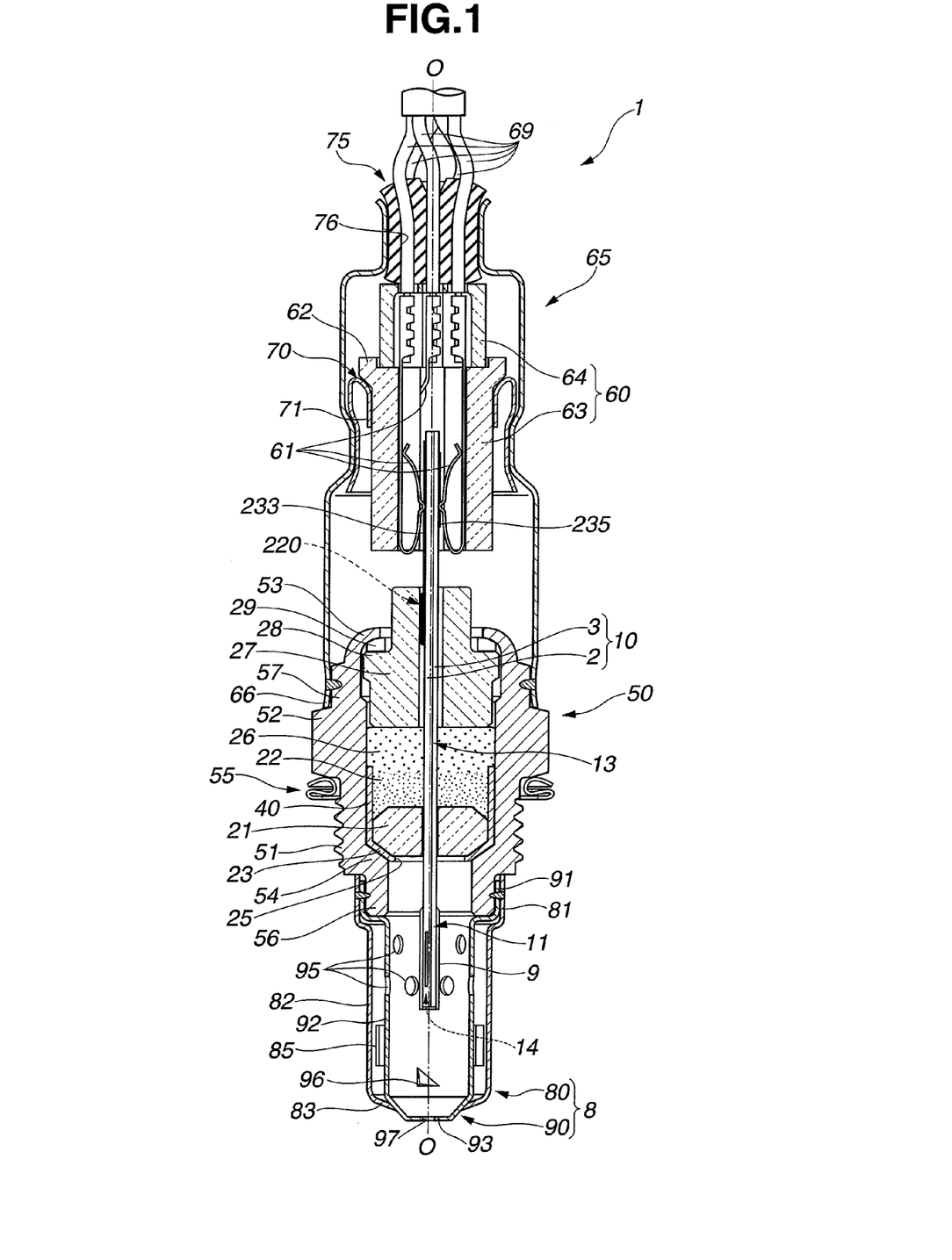
FIG. 1 is a sectional view of a gas sensor (viz., oxygen sensor) according to the present invention.
Figure 2:
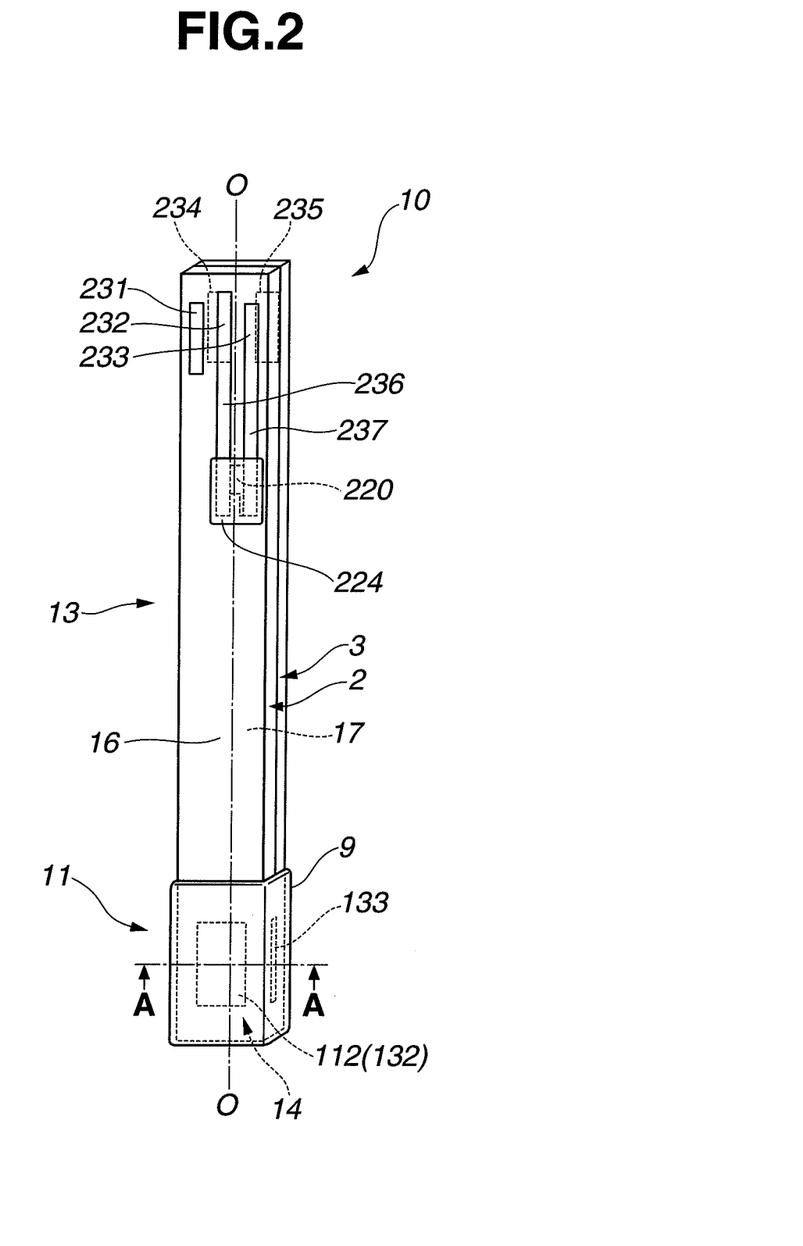
FIG. 2 is a perspective view of a gas sensor element installed in the gas sensor according to the present invention.
Figure 3:
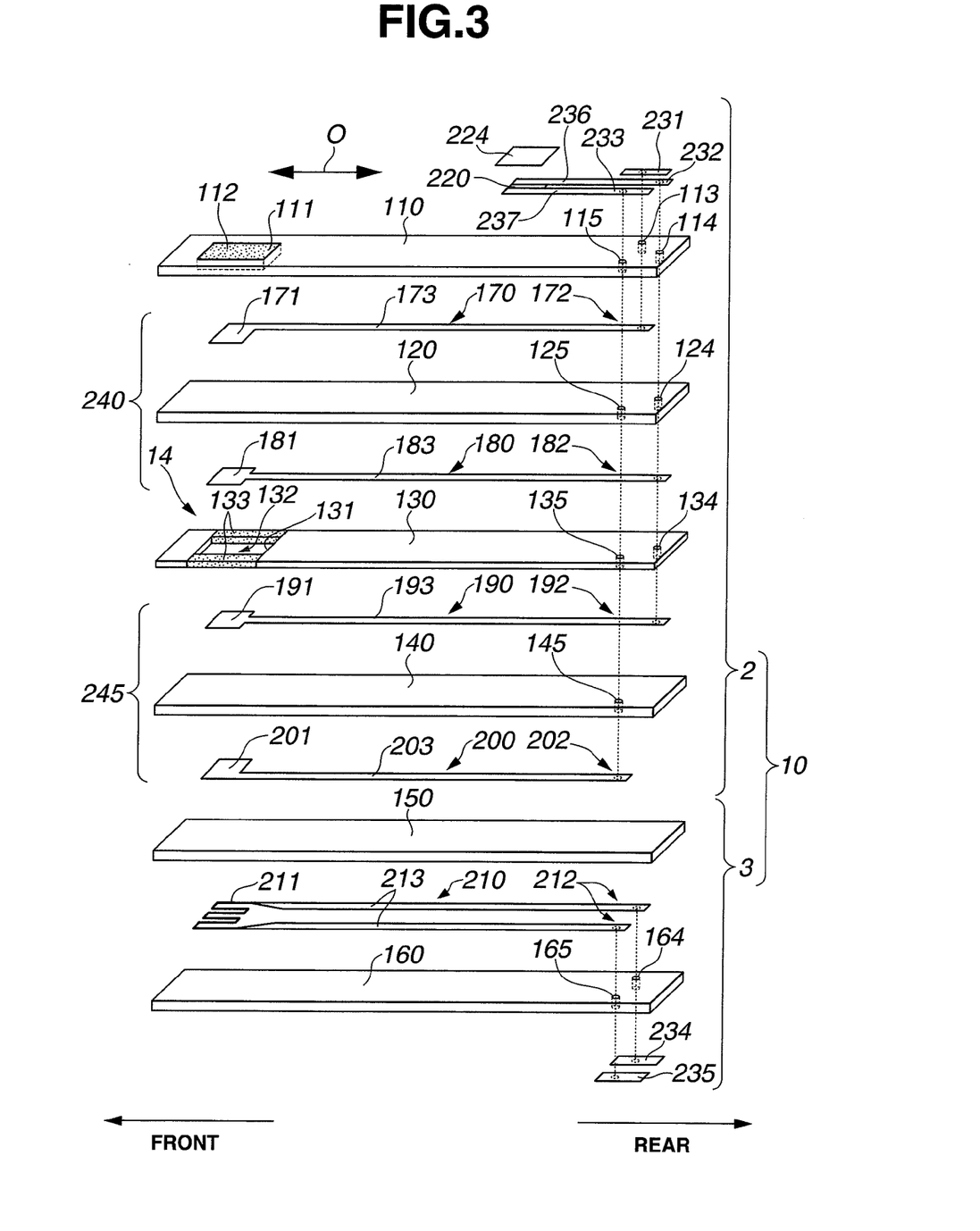
FIG. 3 is an exploded perspective view of the gas sensor element of FIG. 2.
Figure 4:
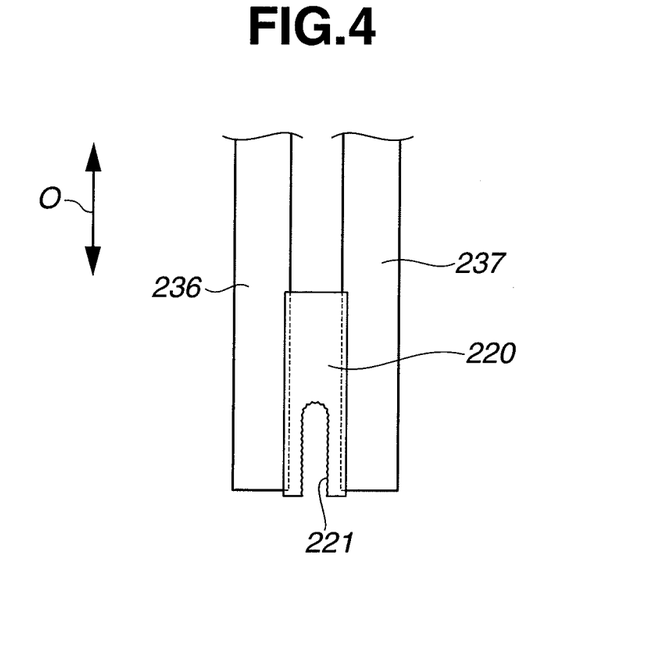
FIG. 4 is an enlarged illustration for explaining a trimming applied to a compensating resistor.

It is to be noted that in FIGS. 1, 2 and 4, an axial direction "O" of the gas sensor 1 is represented by a vertical direction and in FIG. 3, the axial direction "O" is represented by a horizontal direction. In FIGS. 1 and 2, the axial direction "O" is depicted by an alternate long and short dash line, and in FIGS. 3 and 4, the axial direction "O" is indicated by an arrow. In FIGS. 1, 2 and 4, a leading portion of the gas sensor 1 is shown at a lower part, and in FIG. 3, the leading portion of the gas sensor 1 is placed at a right part. Thus, an end portion of the gas sensor 1 is placed at a part opposite to the above-mentioned part in each figure.

Referring back to FIG. 1, the gas sensor 1 shown is an oxygen sensor, more specifically, a full-range air/fuel ratio sensor that is to be fixed to an exhaust tube of a motor vehicle to sense the oxygen in an exhaust gas issued from an internal combustion engine mounted to the motor vehicle, more specifically, to issue information for obtaining an air/fuel ratio of the exhaust gas.

As shown, the oxygen sensor 1 installs therein a sensor element 10 that outputs an information signal representative of an oxygen concentration in the exhaust gas. As will be described in detail hereinafter, the detected information signal is processed by an after-mentioned sensor control unit 250 to provide an information on the air/fuel ratio of the exhaust gas. The information on the air/fuel ratio is processed by an after-mentioned electronic control unit (ECU) 280 for practically carrying out an air/fuel ratio feedback control to the internal combustion engine.

As is seen from FIGS. 1 and 2, the sensor element 10 of the oxygen sensor 1 comprises an elongate plate-shaped detecting element 2 and an elongate plate-shaped heater 3 which are put on each other and extend in the axial direction "O". It is to be noted that a horizontal direction in FIG. 1 corresponds to a direction of the thickness of the element 2 and heater 3, and a direction perpendicular to the horizontal direction corresponds to a direction of the width of the element 2 and heater 3.

In the following description, the sensor element 10 will be explained as a unit that includes both the detecting element 2 and the heater 3. However, if desired, the sensor element 10 may be constructed by only the detecting element 2.

As shown in FIG. 1, the sensor element 10 is tightly held by a metal cap 40 through an after-mentioned insulation and tightening structure, and the metal cap 40 is tightly held by a main cylindrical holder 50. Although not shown in the drawing, the main cylindrical holder 50 is connected to an exhaust tube that extends from the internal combustion engine. The detailed construction of the sensor element 10 will be described hereinafter.

As is seen from FIGS. 1 and 2, at a front end portion 11 of the sensor element 10, there is provided a detecting portion 14 that actually detects the concentration of oxygen. A major portion 13 of the sensor element 10, which extends rearwards from the detecting portion 14, is tightly installed in the main cylindrical holder 50, as shown in FIG. 1.

As is seen from FIG. 1, a front part of the major portion 13 is held by the metal cap 40 through the insulation and tightening structure. That is, the metal cap 40 is a holding member for tightly holding the sensor element 10 in the main cylindrical holder 50. As shown, from a front opening 25 of the metal cap 40, there extends the leading end portion 11 of the sensor element 10. A front end portion 23 of the metal cap 40 that defines the front opening 25 is tapered as shown.

Within the metal cap 40, there are coaxially installed a ceramic ring 21 of alumina and a talc ring 22 of compressed talcum powder. As shown, these rings 21 and 22 have coaxial bores through which the sensor element 10 passes. The talc ring 22 is tightly installed and intimately compressed in the metal cap 40 thereby to achieve an assured positioning of the sensor element 10 relative to the metal cap 40.

As shown in FIG. 1, the sensor element 10 having the metal cap 40 united thereto is tightly held by the main cylindrical holder 50.

As is described hereinabove, the main cylindrical holder 50 is a member for tightly connecting the oxygen sensor 1 to an exhaust tube extending from an internal combustion engine. For this reason, the main cylindrical holder 50 is formed at a front portion thereof with an external thread 51 that is to be engaged with an internal thread (not shown) provided by the exhaust tube from the internal combustion engine. The front portion of the holder 50 is further formed at a front end thereof with a front engaging part 56 to which an after-mentioned protecting tube 8 is secured.

As shown in FIG. 1, the main cylindrical holder 50 is formed, at and around a middle portion thereof, with a polygonal projection (viz., polygonally annular projection) 52 that is engageable with a handling tool (not shown). That is, by turning the oxygen sensor 1 about the axis "O" with the aid of the handling tool engaged with the polygonal projection 52, the oxygen sensor 1 can be secured to the exhaust tube.

Between a front end of the polygonal projection 52 and a rear end of the external thread 51, there is disposed an annular gasket 55 that achieves a seal of the engagement between the external thread 51 of the main cylindrical holder 50 and the internal thread provided by the exhaust tube.

As shown, the polygonal projection 52 is further formed at a rear part thereof with both a rear engaging portion 57 that is engaged with an after-mentioned outer cylindrical housing 65 and a crimped portion 53 that is crimped to tightly hold the sensor element 10 in the main cylindrical holder 50. It is thus to be noted that the holder 50 can serves as a housing.

As shown in FIG. 1, the cylindrical inner surface of the holder 50 is formed, near the external thread 51, with a tapered area 54 to which the front end portion 23 of the metal cap 40 is engaged and pressed.

Within the holder 50, there is tightly disposed another talc ring 26 that, having the sensor element 10 passed therethrough, is put into the metal cap 40 from the rear open end of the metal cap 40. Furthermore, within the holder 50, there is tightly disposed a cylindrical sleeve 27 in a manner to press the talc ring 26 from the back. The cylindrical sleeve 27 is formed at a rear portion thereof with a shoulder part 28. Between the shoulder part 28 and the above-mentioned crimped portion 53 of the holder 50, there is tightly disposed an annular swaging packing 29. That is, by applying swaging to the portion 53, the cylindrical sleeve 27 is pressed toward the talc ring 26 and presses the talc ring 26. With such compression force, the talc ring 26 is smashed in the holder 50 to establish a fine and intimate packing of talcum powder in the holder 50. With the talc ring 26 thus smashed and the talc ring 22 previous set, both the metal cap 40 and the sensor element 10 are hermetically held in the main cylindrical holder 50.

As shown in FIG. 1, the front engaging part 56 of the holder 50 is shaped cylindrical and has a cylindrical protector unit 8 fixed thereto. The protector unit 8 surrounds the leading end portion 11 of the sensor element 10 to protect the end portion 11 from foreign materials. That is, due to provision of the protector unit 8, the leading end portion 11 is protected from water and protected from being damaged by foreign material. For securing the protector unit 8 to the front engaging part 56, spot welding, laser welding or the like is used. The cylindrical protector unit 8 has a double tube construction comprising a cylindrical bottomed inner protector 90 and a cylindrical outer protector 80 that concentrically surrounds the inner protector 90 leaving a cylindrical space therebetween.

As is seen from FIG. 1, the inner protector 90 is formed at a rear half portion of a cylindrical wall 92 thereof with a plurality of gas inlet openings 95, at a front end portion of the cylindrical wall 92 with a plurality of water discharging openings 96 and at a front end thereof (viz., a bottom wall 93) with a gas outlet opening 97. A rear open end 91 of the inner protector 90 is enlarged in diameter and tightly disposed on the front engaging part 56 of the main cylindrical holder 50.

As shown, the cylindrical outer protector 80 is formed at a cylindrical wall 82 thereof with a plurality of gas inlet openings 85. A rear open end 81 of the outer protector 80 is enlarged in diameter and tightly disposed on the rear open end 91 of the inner protector 90. For securing the rear open ends 81 and 91 of the two protectors 80 and 90 to the front engaging part 56 of the holder 50, a laser welding is used, which is practically applied around the rear open end 81 of the outer protector 80. As shown, a front end portion 83 of the outer protector 80 is tapered to contact with the front end portion of the inner protector 90. With such contact, the cylindrical space defined between the two cylindrical protectors 80 and 90 is closed except the openings 85, 95 and 96.

As shown in FIG. 1, a rear end portion of the major portion 13 of the sensor element 10 projects rearward from the rear end of the main cylindrical holder 50.

As is seen from FIGS. 1, 2 and 3, on the major portion 13 of the sensor element 10, there are provided five electrode pads 231, 232, 233, 234 and 235 that are made of platinum (Pt).

As will be understood from FIG. 1, in practical use, the five electrode pads 231 to 235 contact with five connecting pins 61 respectively to energize the detecting element 2 and the heater 3. As shown, each connecting pin 61 has a bent back front part. The rear end part of the major portion 13 of the sensor element 10 is equipped with a cylindrical separator 60 that is constructed of insulative ceramic. The cylindrical separator 60 has therein five connecting pins 61 that are in contact with the bent back front parts of the electrode pads 231 to 235 respectively.

The cylindrical separator 60 comprises a front separator part 63 and a rear separator part 64. A circular front end of the rear separator part 64 is tightly put in a circular recess (no numeral) defined by an annular ridge 62 formed on a rear end of the front separator part 63. Within the front separator part 63, there are arranged the five electrode pads 231 to 235 and the five connecting pins 61 in such a manner that each electrode pad 231, 232, 233, 234 or 235 contacts to the bent back front part of corresponding one of the five connecting pins 61. Of course, each contacting pair including one electrode pad and a corresponding connecting pin 61 is suppressed from contacting neighboring contacting pair.

Within the rear separator part 64, there are installed wire grasping portions of the five connecting pins 61 by which five lead wires 69 are tightly grasped. As is seen from FIG. 5, the five lead wires 69 extend to the sensor control unit 250.

Referring back to FIG. 1, the outer cylindrical housing 65 is constructed of stainless steel (for example, SUS 304 in Japanese Industrial Standard). As shown, the outer cylindrical housing 65 is fixed to the rear end portion of the main cylindrical holder 50 and covers the exposed major portion 13 of the sensor element 10 and the separator 60. That is, a front open end 66 of the outer cylindrical housing 65 is tightly put on the rear engaging portion 57 of the main cylindrical holder 50. For achieving a secured connection between the front open end 66 and the rear engaging portion 57, the front open end 66 is crimped and a laser welding is applied to and around the front open end 66.

Between the outer cylindrical housing 65 and the front separator part 63, there is disposed an annular resilient holder 70 which is constructed of a thin metal. The annular resilient holder 70 has a rear portion 71 bent inward. As shown, upon setting of the holder 70, the inward bent rear portion 71 is pressed against a back side of the annular ridge 62 of the front separator part 63 thereby to resiliently support the front separator part 63 in the outer cylindrical housing 65. For assuring the setting of the holder 70, a middle portion of the cylindrical housing 65 that contacts to the holder 70 is crimped as shown. Thus, the front separator part 63 is assuredly and resiliently held in the outer cylindrical housing 65 through the holder 70.

Within an opening formed in a rear end of the outer cylindrical housing 65, there is tightly set a grommet 75 of fluorocarbon rubber. The grommet 75 is formed with five openings 76 through which the five lead wires 69 from the rear separator part 64 pass in an air-tight manner, as shown. For assuring the setting of the grommet 75, the rear end of the housing 65 that contacts to the grommet 75 is crimped as shown. With this, the grommet 75 is tightly held by the rear open end of the housing 65.

In the following, the description will be directed to the sensor element 10 with the aid of FIGS. 2 and 3.

First, the outline of the sensor element 10 will be described.

As is seen from FIG. 2, the sensor element 10 comprises the elongate plate-shaped detecting element 2 and the elongate plate-shaped heater 3 which are put on each other and extend in the axial direction "O". More specifically, these two flat members 2 and 3 are put on each other in the direction of their thickness.

As is seen from FIGS. 2 and 3, the detecting portion 14 provided on the front end portion 11 of the sensor element 10 has, as a main element, a gas detecting chamber 132 (see FIG. 3) that is formed in the elongate plate-shaped detecting element 2. In operation, the exhaust gas from the engine is led into the gas detecting chamber 132 and subjected to an oxygen concentration measurement. As is seen from FIGS. 1 and 2, around the front end portion of the sensor element 10 including the detecting portion 14, there extends a porous protecting layer 9.

As is seen from FIG. 2, on an upper part of an external flat surface 16 of the elongate plate-shaped detecting element 2, there are disposed the three electrode pads 231, 232 and 233 which are in contact with three of the five connecting pins 61. It is to be noted that in FIG. 1, the three connecting pins 61 are shown in a left side of the sensor element 10.

As is understood from FIG. 3, on an upper part of an external flat surface of the elongate plate-shaped heater 3, there are disposed the two electrode pads 234 and 235 which are in contact with two of the five connecting pins 61. It is to be noted that in FIG. 1, the two connecting pins 61 are shown in a right side of the sensor element 10.

Referring back to FIG. 2, on the external flat surface 16 of the elongate plate-shaped detecting element 2, there is printed a compensating resistor 220 constructed of a material such as uthenium tetroxide or the like that is relatively low in a resistance temperature coefficient. For the printing, a so-called pattern printing technique is used. Two electrode leads 236 and 237 connected to opposed ends of the compensating resistor 220 are connected to the above-mentioned electrode pads 232 and 233.

The compensating resistor 220 is lined or covered with a protecting layer 224 constructed of a ceramic, glass or the like. With such protecting layer 224, the compensating resistor 220 is protected from surrounding gases. It is to be noted that due to provision of the protecting layer 224, undesired contact between the compensating resistor 220 and the surrounding gases is assuredly prevented, and thus, the resistor 220 is suppressed from having substantial effect from the gases, particularly, the temperature of the same. Thus, as will be described in detail hereinafter, the resistance value of the compensating resistor 220 can be obtained with much higher accuracy.

Second, the detail of the sensor element 10 will be described in the following with the aid of FIG. 3.

As is seen from FIG. 3, the sensor element 10 comprises the elongate plate-shaped detecting element 2 and the elongate plate-shaped heater 3 which are put on each other and extend in the direction of the arrow "O".

The detecting element 2 comprises an insulative substrate 110 composed almost exclusively of alumina, a solid electrolyte substrate 120 composed almost exclusively of zirconia, an insulative substrate 130 composed almost exclusively of alumina and a solid electrolyte substrate 140 composed almost exclusively of zirconia which are put on one another in order, that is, in the illustrated manner.

The solid electrolyte substrate 120 has on its both surfaces current carrying patterns 170 and 180 respectively. Like this, the other solid electrolyte substrate 140 has on its both surfaces current carrying patterns 190 and 200 respectively. Each current carrying pattern 170, 180, 190 or 200 is constructed of platinum.

As shown in FIG. 3, the current carrying pattern 170 provided on the upper surface of the solid electrolyte substrate 120 comprises a lead part 173 that extends from the front side of the solid electrolyte substrate 120 to the rear side of the same, and the current carrying pattern 170 has an enlarged electrode part 171 at the front side of the substrate 120. The insulative substrate 110 is put on the upper surface of the solid electrolyte substrate 120 having the current carrying pattern 170 intimately put therebetween, as shown. The insulative substrate 110 has, at a rear end portion thereof that faces a rear end portion 172 of the current carrying pattern 170, a through hole 113.

As shown in FIG. 3, on the rear end surface portion of the insulative substrate 110 at the position of the through hole 113, there is provided the above-mentioned electrode pad 231. This electrode pad 231 is electrically connected to the rear end portion 172 of the current carrying pattern 170 through a conducting member provided in the through hole 113.

As shown, at the front end portion of the insulative substrate 110 at the position facing the enlarged electrode part 171, there is formed a rectangular opening 111. In the rectangular opening 111, there is received a porous layer 112 composed almost exclusively of alumina. Thus, the enlarged electrode part 171 of the current carrying pattern 170 is exposed to the gaseous environment through the porous layer 112.

As shown in FIG. 3, the current carrying pattern 180 provided on the lower surface of the solid electrolyte substrate 120 comprises a lead part 183 that extends from the front side of the solid electrolyte substrate 120 to the rear side of the same, and like the above-mentioned current carrying pattern 170, the current carrying pattern 180 has an enlarged electrode part 181 at the front side of the substrate 120. The enlarged electrode part 181 and the above-mentioned enlarged electrode part 171 are placed at opposed positions with respect to the solid electrolyte substrate 120.

The electrode parts 171 and 181 having the solid electrolyte substrate 120 intimately put therebetween thus constitute an oxygen pump cell (IP cell) 240 that carries out an oxygen pumping.

The insulative substrate 110 and solid electrolyte substrate 120 have, at their rear end portions at positions corresponding to a rear end portion 182 of the current carrying pattern 180, respective through holes 114 and 124.

As shown in FIG. 3, on the rear end surface portion of the insulative substrate 110 at the position of the through hole 114, there is provided the above-mentioned electrode pad 232. The electrode pad 232 is placed beside the above-mentioned electrode pad 231 keeping a parallel arrangement therebetween with respect to the axial direction "O" of the sensor element 10. The electrode pad 232 is electrically connected to the rear end portion 182 of the current carrying pattern 180 through a conduction member provided in the through hole 114 and another conducting member provided in the through hole 124.

As is seen from FIG. 3, the other insulative substrate 130 is put on the lower surface of the solid electrolyte substrate 120 having the current carrying pattern 180 intimately put therebetween.

At the front end portion of the insulative substrate 130 at the position facing the enlarged electrode part 181, there is formed a rectangular opening 131. The rectangular opening 131 is closed by the two solid electrolyte substrates 120 and 140 that are put on the upper and lower surfaces of the insulative substrate 130 respectively. With this closing, the rectangular opening 131 functions as the gas detecting chamber 132.

The enlarged electrode part 181 of the current carrying pattern 180 is exposed to the gas detecting chamber 132.

As will be understood from FIG. 2, the gas detecting chamber 132 constitutes a main part of the oxygen detecting portion 14 for detecting (or measuring) the concentration of oxygen in the exhaust gas.

Referring back to FIG. 3, the rectangular opening 131 of the insulative substrate 130 is provided at lateral sides thereof with diffusion rate-determining portions 133 respectively. Each diffusion rate-determining portion 133 is composed of a porous body of alumina. Thus, the surrounding exhaust gas is permitted to enter the gas detecting chamber 132 through the diffusion rate-determining portions 133.

The solid electrolyte substrate 140 is put on the lower surface of the insulative substrate 130. On the upper surface of the solid electrolyte substrate 140, there is provided the current carrying pattern 190 which, like the above-mentioned current carrying pattern 170, comprises a lead part 193 that extends from the front side of the substrate 140 to the rear side of the same, and the current carrying pattern 190 has an enlarged electrode part 191 at the front side of the substrate 140. Also the enlarged electrode part 191 is exposed to the gas detecting chamber 132.

As is seen from FIG. 3, the insulative substrate 130 has, at its rear end portion facing a rear end portion 192 of the lead part 193 of the current carrying pattern 190, a through hole 134. The position where the through hole 134 is provided faces the rear end portion 182 of the above-mentioned current carrying pattern 180, as shown. The rear end portion 182 of the lead part 183 of the current carrying pattern 180 and the rear end portion 192 of the lead part 193 of the other current carrying pattern 190 are electrically connected through a conducting member provided in the through hole 134. That is, the current carrying pattern 180, the other current carrying pattern 190 and the electrode pad 232 are electrically connected.

On the lower surface of the solid electrolyte substrate 140, there is provided a current carrying pattern 200 that constitutes a pair with the above-mentioned pattern 190. Like the pattern 190, the current carrying pattern 200 comprises a lead part 203 that extends from the front side of the solid electrolyte substrate 140 to the rear side of the same, and the pattern 200 has an enlarged electrode part 201 at the front side of the substrate 140. As shown, the enlarged electrode part 201 is placed at a position opposite to the position of the enlarged electrode part 191 of the pattern 190 with respect to the substrate 140. The two electrode parts 191 and 201 and the solid electrolyte substrate 140 constitute a so-called oxygen generating cell "VS cell" 245 (see FIG. 5) that generates oxygen.

As shown, on the rear end portion of the upper surface of the insulative substrate 110, there is provided the electrode pad 233 that is arranged in parallel with the neighboring pads 231 and 232.

A rear end 202 of the lead part 203 of the current carrying pattern 200 takes a position as mated with the electrode pad 233, as shown. Between the rear end 202 of the current carrying pattern 200 and the electrode pad 233, there are sandwiched respective rear end portions of the solid electrolyte substrate 140, insulative substrate 130, solid electrolyte substrate 120 and insulative substrate 110, which have respective aligned through holes 145, 135, 125 and 115. The rear end 202 of the current carrying pattern 200 and the electrode pad 233 are electrically connected through conducting members provided in the through holes 145, 135, 125 and 115.

As is seen from FIG. 3, on the upper rear surface of the insulative substrate 110 at a position near a middle portion of the substrate 110, there is provided the compensating resistor 220. The position of this resistor 220 will be clearly understood from FIG. 2. The compensating resistor 220 extends in the axial direction "O" direction of the insulative substrate 110. As shown in FIG. 2, the above-mentioned electrode leads 236 and 237 are connected to opposed ends of the compensating resistor 220. The electrode leads 236 and 237 extend axially to the rear end portion of the insulative substrate 110 to connect to the electrode pads 232 and 233 respectively. The upper surface of the insulative substrate 110 is provided with a protecting layer 224 that covers the compensating resistor 220.

In the following, the detailed construction of the heater 3 will be described with the aid the drawings, particularly FIG. 3.

As is seen from FIG. 3, the heater 3 comprises a heat generating resistor 210 of platinum that is intimately put between two insulative substrates 150 and 160 which are composed almost exclusively of alumina. The heat generating resistor 210 is of a current carrying pattern that has opposed ends. The heat generating resistor 210 comprises a main heat generating part 211 that has a reduced cross section for effective heat generation and is arranged at the front end portion 11 of the sensor element 10 (see FIG. 2).

As is seen from FIG. 3, two lead portions 213 extending from the main heat generating part 211 have each a larger cross section than the main part 211. The two lead portions 213 extend in the axial direction toward the rear ends of the insulative substrates 150 and 160.

As shown in FIG. 3, on a right end portion of a lower surface of the insulative substrate 160, there are provided the electrode pads 234 and 235 which are arranged side by side with respect to the axial direction "O". As is seen from FIG. 2, these two electrode pads 234 and 235 are arranged at a surface of the sensor element 10 opposite to the surface on which the two electrode pads 231, 232 and 233 are arranged.

Referring back to FIG. 3, the two electrode pads 234 and 235 are electrically connected to rear ends 212 of the two lead portions 213 of the heat generating resistor 210 through conducting members provided in through holes 164 and 165 formed in the insulative substrate 160. As shown, the heater 3 is intimately put on the detecting element 2 to constitute the sensor element 10.

As is understood from FIG. 2, the compensating resistor 220 is arranged on the external flat surface 16 of the major portion 13 of the sensor element 10.

The compensating resistor 220 functions to compensate for variation in the oxygen concentration detecting characteristic of the sensor element 10. As is known, the sensor elements 10 have inevitable characteristics. By the compensation, the outputs of the sensor element 10 are those that have been provided with respect to correcting information (viz., correction factor "K" as will be mentioned hereinafter) prepared for each sensor element 10.

Both ends of the compensating resistor 220 are respectively connected to the electrode leads 236 and 237 which are connected to the electrode pads 232 and 233 respectively.

Figure 5:
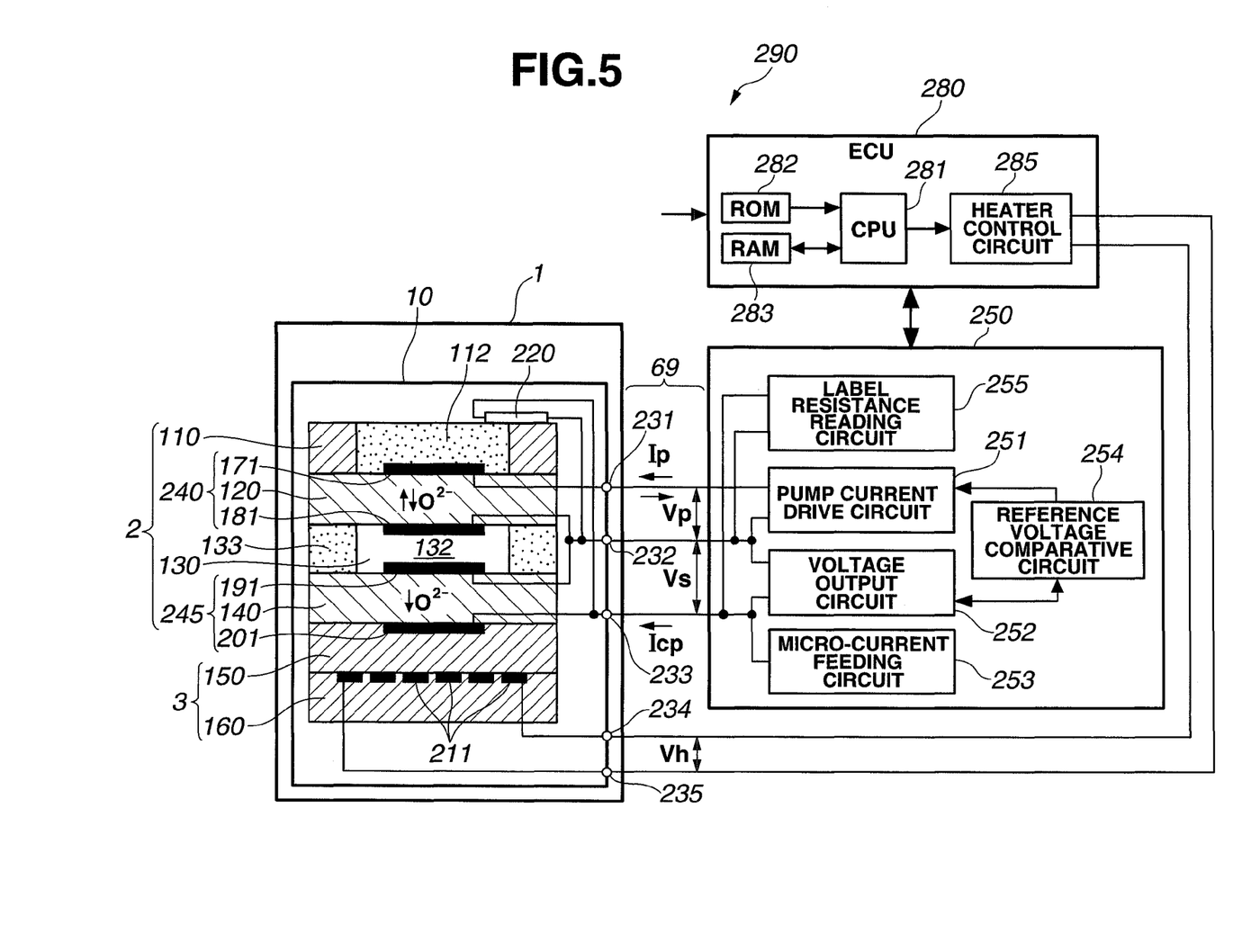
FIG. 5 is a block diagram of a control system practically employed in the present invention.

As is mentioned hereinabove, the electrode pads 232 and 233 are connected to the current carrying patterns 190 and 200. That is, the compensating resistor 220 is connected to paired current flow lines through which current feeding to the paired electrode parts 191 and 201 of the VS cell 245 is made, and the compensating resistor 220 is connected to the VS cell 245 in a parallel manner.

The electrode pads 232 and 233 and the compensating resistor 220 are directly connected through the electrode leads 236 and 237. That is, the current flow lines for connecting the electrode pads 232 and 233 to the compensating resistor 220 are constituted by only the electrode leads 236 and 237 respectively. In short, the solid electrolyte substrates 120 and 140 don't take part in constituting the current flow lines. More specifically, the current flow lines to the compensating resistor 220 have no electric connection with the solid electrolyte substrate 120 and no electric connection with current flow lines to the solid electrolyte substrates 120 and 140. The current flow lines to the compensating resistor 220 and those to the solid electrolyte substrates 120 and 140 are completely isolated.

Accordingly, even if the solid electrolyte substrates 120 and 140 are subjected to a marked value difference in resistance due to temperature change or the like, information on the resistance value of the compensating resistor 220 is ideally obtained without being affected by the resistance value difference of the solid electrolyte substrates 120 and 140.

The solid electrolyte substrate 120 or 140 shows insulation at a low temperature including room temperature, and when it is heated up to a working temperature higher than an activating temperature (for example, 600° C.), it shows an oxygen ion conductivity.

In the present invention, the compensating resistor 220 is constructed to show a resistance value that is lower than a resistance value which is shown by the solid electrolyte substrate 140 of the VS cell 245 under a room temperature condition, and shows a resistance value which is more than ten times as much as a resistance value which is shown by the solid electrolyte substrate 140 under a condition of activating or working temperature (for example, 800° C.). The resistance value of the compensating resistor 220 is varied by changing the material and size of the same. More specifically, in the invention, for producing the compensating resistor 220, a known production technique is applied to ruthenium tetroxide.

Thus, when, under a room temperature, a suitable voltage is applied between the electrode pads 232 and 233, current is permitted to flow in the compensating resistor 220. However, under such room temperature, the current does not flow in the solid electrolyte substrate 140 (or VS cell 245) because the solid electrolyte substrate 140 shows insulation (viz., non-conductance) under such room temperature. Accordingly, the resistance value of the compensating resistor 220 can be read.

When, under working temperature, a suitable voltage is applied between the electrodes 232 and 233, current is permitted to flow in the solid electrolyte substrate 140 that shows an oxygen ion conductivity. However, in this case, the current fails to flow in the compensating resistor 220 because it shows the remarkably high resistance value as compared with that of the solid electrolyte substrate 140. Actually, a very small current is permitted to flow in the compensating resistor 220. Thus, the VS cell 245 can be driven or operated. It is to be noted that since the resistance value of the solid electrolyte substrate 140 (viz., the resistance value of the VS cell 245) is quite small as compared with that of the compensating resistor 220, the compensating resistor 220 connected in parallel to the VS cell 245 has no influence on the operation of the VS cell 245.

In order to reflect a correction information in the compensating resistor 220, it is necessary to adjust the resistance value of the compensating resistor 220 for each sensor element 10.

In the present invention, adjustment of the resistance value of the compensating resistor 220 is made through a known trimming that uses LASER. That is, after production of the sensor element 10, LASER trimming is practically applied to the compensating resistor 220.

One of the methods of such trimming is depicted in FIG. 4. In this method, part of the pattern of the compensating resistor 220 is cut in the axial direction "O" by LASER so that a resisting body connecting the two leads 236 and 237 has an elongate cut 221. In this method, the resistance value (or electric resistance) between the leads 236 and 237 increases as the length of the cut 221 increases.

Adjustment of the resistance value for the compensating resistor 220 will be described in the following.

First, the sensor element 10 is set in an enclosed space in which a gas with a predetermined oxygen concentration is contained. For example, the gas may be atmospheric air. Then, under flowing of a pump current "Ip" to the sensor element 10, a signal (or detected signal) produced or issued by the sensor element 10 is obtained and calculation of correction factor is carried out to cause the detected signal to have a target or to desired value. Then, in view of a relationship between the correction factor and the resistance value of the compensating resistor 220, a resistance value (viz., set resistance value) to be set for the compensating resistor 220 is found out or derived.

Then, cutting work for making the elongate cut 221 is carried out while monitoring that the resistance value of the compensating resistor 220 comes to the set resistance value. With these steps, the compensating resistor 220 can have a set resistance value that is in conformity with the sensor element 10 in which the resistor 220 is provided. By carrying out these steps, the resistance value of the compensating resistor 220 (viz., the resistance value between the electrode leads 236 and 237 connected to both ends of the resistor 220) can be easily adjusted at will. Of course, high accuracy is expected. Of course, after the trimming, under a condition of room temperature, the resistance value of the compensating resistor 220 should show a value that is lower than a resistance value of the solid electrolyte substrate 140, and under a condition of working temperature, for example 800° C., the resistance value of the compensating resistor 220 should show a resistance value that is more than ten times as much as the resistance value of the solid electrolyte substrate 140.

Referring back to FIGS. 2 and 3, the protecting layer 224 is applied to the compensating resistor 220 before the trimming of the resistor 220. That is, during the LASER trimming, the protecting layer 224 is also dissolved forming an elongate cut. With the trimmed protecting layer 224, a suitable compressive stress can be applied to the compensating resistor 220. Actually, due to such applied compressive stress, the compensating resistor 220 is prevented from being cracked by a tensile stress that would be applied to the compensating resistor 220 when it is heated.

As is seen from FIG. 5, the oxygen sensor 1 having the above-mentioned sensor element 10 is connected to a sensor control unit 250. An electrical control unit "ECU" 280 operates the sensor control unit 250. That is, in accordance with programmed operation steps executed by the electrical control unit 280, the oxygen sensor 1 is driven.

In the following, an entire control system 290 including the oxygen sensor 1, the sensor control unit 250 and the electrical control unit 280 will be described in detail with the aid of FIG. 5.

It is to be noted that a sectional view of the sensor element 10 shown in FIG. 5 is a schematic view taken along the line A-A of FIG. 2.

As shown in FIG. 5, the sensor control unit 250 comprises a pump current drive circuit 251, a voltage output circuit 252, a micro-current feeding circuit 253, a reference voltage comparative circuit 254 and a label resistance reading circuit 255.

As is mentioned hereinabove, the oxygen sensor 1 is connected to the above-mentioned circuits of the sensor control unit 250 through leads 69 connected to the electrode pads 231 to 235 of the sensor element 10. Furthermore, the sensor control unit 250 is connected to the electrical control unit "ECU" 280 through a communication circuit (not shown), so that the drive condition of the above-mentioned circuits is controlled by instruction signals issued from the electrical control unit 280.

The micro-current feeding circuit 253 functions to feed the VS cell 245 with a given amount of micro-current "Icp" in the direction from the electrode part 201 to the electrode part 191. The micro-current feeding circuit 253 is connected to the electrode pad 233 of the sensor element 10, so that due to the flow of the micro-current "Icp" by the circuit 253, oxygen is sucked into the side of the electrode part 201 causing the electrode part 201 to serve as a so-called oxygen reference electrode.

The voltage output circuit 252 functions to detect an electromotive force "Vs" generated between the electrode parts 191 and 201 of the VS cell 245. For this, the voltage output circuit 252 is connected to the electrode pads 233 and 232 of the sensor element 10.

The reference voltage comparative circuit 254 functions to compare a reference voltage (viz., 450 mV in the invention) with the electromotive force "Vs" detected by the voltage output circuit 252 and feeds back the results of the comparison to the pump current drive circuit 251.

Upon receiving the results of the comparison from the circuit 254, the pump current drive circuit 251 controls the amount and flowing direction of the pump current "Ip" fed to the oxygen pump cell (IP cell) 240, and thus, the pump current drive circuit 251 is connected to the electrode pads 231 and 232.

The label resistance reading circuit 255 functions to read, from the compensating resistor 220 of the sensor element 10, the resistance value that has been reflected by the correction information (viz., correction factor K). As has been mentioned hereinabove, the compensating resistor 220 is connected to the paired current flow lines through which current is led to the electrodes 191 and 201 of the VS cell 245, and thus the compensating resistor 220 is connected to the VS cell 245 in parallel. In order to read the resistance value of the compensating resistor 220, the label resistance reading circuit 255 is connected in parallel to connecting lines (viz., a pair of current feeding lines for causing current to flow to the paired electrodes 191 and 201) of the electrode pads 232 and 233 of the sensor element 10. The reading of the resistance value of the compensating resistor 220 is carried out in accordance with a sensor control program which will be described hereinafter. In the invention, by feeding a given amount of micro-current "Icp" to the compensating resistor 220, the resistor 220 is caused to issue a voltage signal, and by processing the issued voltage signal and the micro-current "Icp", the resistance value of the compensating resistor 220 is obtained.

As is seen from FIG. 5, the electrical control unit "ECU" 280 comprises a central processing unit (CPU) 281, a read only memory (ROM) 282, a random access memory (RAM) 283 and a heater control circuit 285. Upon receiving various information signals such as those from the sensor control unit 250 and those related to operation of an associated motor vehicle (for example, information signals on engine cooling water temperature, engine speed, etc.,), the electric control unit "ECU" 280 excuses predetermined programs (viz., programmed operation steps) to control operation of various devices, such as the engine and an external device, in accordance with the received information signals. Aftermentioned sensor control program is one of the predetermined programs. Initial values used for such programs are stored in the read only memory (ROM) 282. A table (or map) and formulas that show relationship between the resistance value of the compensating resistor 220 and the correction factor "K" are also stored in the read only memory (ROM) 282.

The heater control unit 285 is a circuit for applying a voltage "Vh" to the heater 3 in cooperation with a known sensor resistance value detecting circuit (not shown). By the sensor resistance value detecting circuit, a given amount of current variation is applied to the VS cell 245 at regular intervals from a current feeding circuit (not shown), and an amount of voltage variation thus obtained by the VS cell 245 is outputted to the electric control unit "ECU" 280 as a sensor resistance value representing signal. By the electric control unit "ECU" 280, the temperature of the sensor element 10 is derived based on the sensor resistance value representing signal and the heater control circuit 285 is operated based on the derived temperature, so as to control the voltage applied to the heater 3 in a so-called PWM m (pulse-width modulation) way. That is, the voltage applied to the heater 3 is so controlled as to cause the sensor element 10 to have the working temperature (for example 800° C.) that is higher than the activating temperature (for example, 600° C.). More specifically, the control is so made as to cause the sensor resistance value to have a target resistance value that is suitable to the working temperature. With such control, the solid electrolyte substrates 120 and 140 are heated up to a temperature higher than the activating temperature. The temperature control process executed by the electrical control unit "ECU" 280 is a known process such as that disclosed in Japanese Laid-open Patent Application (Tokkai) 2003-185626.

In the following, brief description will be directed to the process for detecting the concentration of oxygen (or air/fuel ratio) contained in the exhaust gas from an internal combustion engine by the sensor element 10 of the oxygen sensor 1.

Under operation of the engine, the IP cell 240 and the VS cell 245 that are provided with the solid electrolyte substrates 120 and 140, which are composed almost exclusively of zirconia, are heated by the heater 3 to become activated. Upon this, a pump current "Ip" fed to the electrodes 171 and 181 of the IP cell 240 is so controlled as to keep the electromotive force generated between the electrodes 191 and 201 at a constant value (for example, 450 mV). Under this, the pump current "Ip" flows in proportion to the concentration of oxygen, and thus, the concentration of oxygen (or air/fuel ratio) in the exhaust gas can be detected or measured linearly based on the pump current "Ip".

As has been mentioned hereinabove, the solid electrolyte substrates 120 and 140 show insulative character at a low temperature including room temperature. By practically using such character, in the invention, the resistance value of the compensating resistor 220 connected in parallel to the VS cell 245 of the detecting element 2 is read. More specifically, in accordance with the sensor control program executed by the UPU 81 disposed in the electrical control unit "ECU" 280, the resistance value of the compensating resistor 220 is read under a condition wherein the solid electrolyte substrates 120 and 140 (or sensor element 10) are under their inactivated condition. As is mentioned hereinabove, after the solid electrolyte substrates 120 and 140 (or sensor element 10) are activated, detected signal (detected value "Vip") based on the pump current "Ip" is obtained and correction of the detected value "Vip" is carried out by using the correction information that is reflected to the resistance value of the compensating resistor 220. Based on the corrected detected value "corrected Vip", the concentration of oxygen and air/fuel ratio in the exhaust gas are derived.

Figure 6:
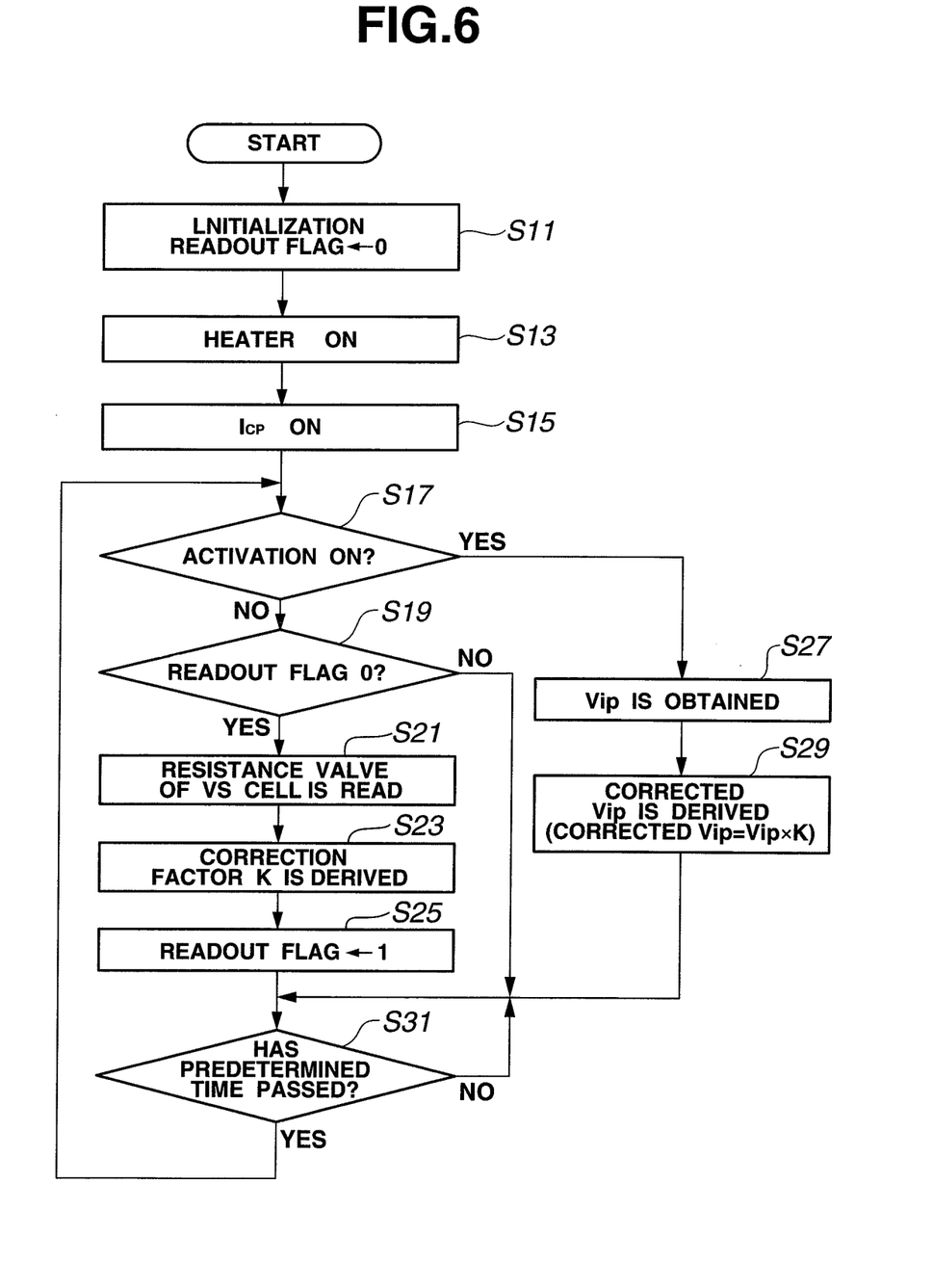
FIG. 6 is a flowchart showing programmed operation steps executed in the control system.

In the following, operation steps of the sensor control program will be described with reference to the flowchart of FIG. 6.

When the engine of the motor vehicle is started, execution of the sensor control program is started in the electrical control unit "ECU" 280.

First, at step S11, initialization is carried out to reset various variables and flags. By the initialization, readout flag for the resistance value of the compensating resistor 220 is set to zero position.

Then, at step S13, the heater control circuit 285 is operated to start energization of the heater 3.

Then, at step S15, a control signal is applied to the sensor control device 250 to cause the micro-current feeding circuit 253 to feed the VS cell 245 with a given amount of micro-current "Icp". With these steps, by the above-mentioned sensor resistance value detecting circuit, a sensor resistance value representing signal is obtained and led into the electrical control unit "ECU" 280.

Then, at step S17, with reference to the temperature of the sensor element 10 that is derived based on the sensor resistance value representing signal, judgment is carried out as to whether activation of the sensor element 10 has been completed or not.

If NO at step S17, that is, if the activation has not been completed yet, the operation flow goes to step S19.

At step S19, judgment is carried out as to whether a readout flag is zero (0) or not, that is, judgment is carried out as to whether it is needed to read the resistance value of the compensating resistor 220 or not. Since the readout flag has been already set to zero (0) at step S11 right after engine starts, the operation flow goes to step S21 while answering "YES".

That is, if YES at step S19, the operation step goes to step S21.

At this step S21, the resistance value of the compensating resistor 220 is read by the label resistance reading circuit 255.

While, if NO at step S19, the operation flow goes to step S31 which will be described in detail hereinafter.

As has been mentioned hereinabove, when the solid electrolyte substrates 120 and 140 (viz., sensor element 10) are in the inactivated condition, they don't show the oxygen ion conductivity. Thus, in this case, the micro-current "Icp" is forced to flow in the compensating resistor 220 that is connected in parallel with the VS cell 245. Accordingly, by reading or detecting the signal (viz., detected value) reflected by the resistance value between the paired electrodes 191 and 201 of the VS cell 245 by the label resistance reading circuit 255, the resistance value of the compensating resistor 220 is obtainable.

It is to be noted that the label resistance reading circuit 255 and the central processing unit (CPU) 281 of the electrical control unit "ECU" 280 that receives through the circuit 255, the signal corresponding to the resistance value of the compensating resistor 220 constitute a so-called first processing means.

As has been described hereinabove, each compensating resistor 220 has been adjusted or trimmed in resistance value in order to match with the correction information (viz., correction factor "K") needed by the corresponding sensor element 10. Accordingly, in the electrical control unit "ECU" 280, the resistance value of the compensating resistor 220 is derived from the corresponding signal that is obtained from the sensor control unit 250 through the label resistance reading circuit 255 and then reference is made to the table (or map) and formulas that show the relationship between the derived resistance value of the compensating resistor 220 and a desired correction factor "K".

That is, at step S23, the desired correction factor "K" is derived.

Then, at step S25, the readout flag is set to one (1). Once the operation flow comes to this step S25, derivation of a new correction factor "K" is suppressed during the engine operation.

Then, the operation flow goes to step S31 which will be described hereinafter.

If YES at step S17, that is, if it is judged that the activation of the sensor element 10 has been completed, the operation flow goes to step S27. That is, when activated, the pump current "Ip" fed to the electrodes 171 and 181 of the IP cell 240 is so controlled as to keep the potential between the electrode parts 191 and 201 of the VS cell 245 at a constant level.

That is, as step S27, by using the sensor control unit 250, a detected signal (detected value "Vip") based on the pump current "Ip" is obtained.

At step S29, a corrected Vip is derived by multiplying the detected value "Vip" by the correction factor "K" that has been obtained at step S23.

By using a known program, the concentration of oxygen in the exhaust gas is calculated based on an exact Vip that is provided by correcting the individual difference of the sensor element 10, and the measured oxygen concentration is practically used for carrying out the air/fuel ratio feedback control of the engine.

At step S31, judgment is carried out as to whether a given time (for example, 10 msec) has passed from the next previous step or not.

If YES at step S31, that is, if it is judged that the given time has passed, the operation flow goes back to step S17 to carry out the above-mentioned steps.

If NO at step S31, that is, if it is judged that the given time has not passed, the judgment of this step repeats.

It is to be noted that the central processing unit (CPU) 281 of the electrical control unit "ECU" 280 that receives the detected signal at step S27 constitutes a so-called second processing means.

It is further to be noted that the central processing unit (CPU) 281 that derives the corrected Vip by multiplying the detected value "Vip" by the correction factor "K" constitutes a so-called third processing means.

As has been mentioned hereinabove, the micro-current "Icp" is forced to flow in the VS cell 245. The micro-current is a constant current. By forcing the constant current to flow through the compensating resistor 220 connected in parallel with the VS cell 245, the resistance value of the corrected resistor is easily obtained.

It is to be noted that the present invention is not limited to the above-mentioned embodiments. Various modifications and variations of such embodiments may be carried out by those skilled in the art, in light of the above description.

Figure 7:
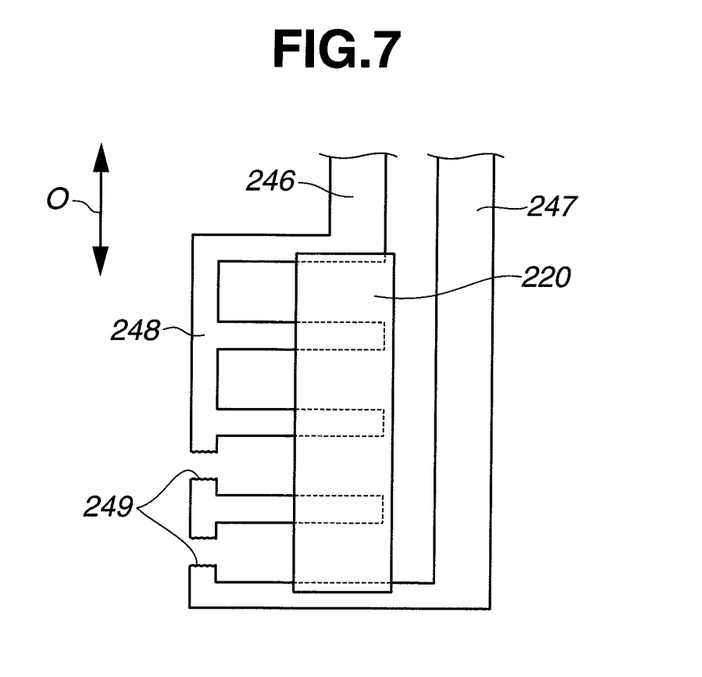
FIG. 7 is an enlarged illustration for explaining another trimming applied to a compensating resistor.

For example, as is seen from FIG. 7, as a substitute for the above-mentioned trimming (viz., Laser trimming) that is applied to a part of the compensating resistor 220, electrode leads 246 and 247 connected to opposed ends of the compensating resistor 220 may have a portion 248 to which the trimming is practically applied. That is, in this example, the trimming is not applied to the compensating resistor 220. As shown in FIG. 7, in this example, the portion 248 is treated to have a comb-shape. Leading portions of teeth of the comb-shaped portion 248 are connected to the compensating resistor 220. LASER trimming is applied to a root portion of the teeth to provide cut portions 249 in the root portion, as shown. With such trimming, the resistance value between the electrode leads 246 and 247 can be adjusted.

In the above, a so-called full-range air/fuel ratio sensor is described as one example of gas sensors. However, in the invention, the sensor is not limited to such sensor. For example, the present invention may be applied to one cell type oxygen sensor that senses the oxygen concentration by practically using the stoichiometric point (14.7) of air/fuel ratio, NOx sensor, HC sensor and the like. Furthermore, in place of the main cylindrical holder 50 (see FIG. 1), holders of a type having no thread may be used.

The entire contents of Japanese Patent Application 2010-045899 filed Mar. 2, 2010 are incorporated herein by reference.

What is claimed is:

1. A gas sensor element for detecting a concentration of oxygen in a gaseous environment and outputting an information signal representative of the concentration of the oxygen, the gas sensor element comprising:
   an elongated plate-shaped detecting element which extends in a lengthwise direction of the gas sensor element, and includes a lower side and an upper side opposing one another, as seen in a thickness direction perpendicular to the lengthwise direction; and
   an elongated plate-shaped heater which extends in the lengthwise direction and is laminated on a surface of the lower side of the elongated plate-shaped detecting element,
   the elongated plate-shaped detecting element including:
      an insulating substrate disposed on the upper side,
      an integrated compensating resistor which is provided on an upper surface of the insulating substrate distally to the elongated plate-shaped heater, and
      at least one pump cell and an oxygen generating cell arranged on a side of the insulating substrate opposite the compensating resistor, each of the at least one pump cell and the oxygen generating cell including a solid electrolyte substrate and a pair of electrodes having the solid electrolyte substrate put therebetween,
   wherein the oxygen generating cell generates the oxygen when a constant current is forced to flow through the paired electrodes of the oxygen generating cell,
   wherein the compensating resistor compensates for a variation in an oxygen concentration detecting result of the gas sensor element and has a resistance value determined in advance according to the oxygen concentration detecting characteristic of the gas senor element which is lower than a resistance value of the solid electrolyte substrate under condition of room temperature and is more than ten times as much as a resistance value of the solid electrolyte substrate under a condition of 800°,
   wherein the resistance value of the compensating resistor reflects correction information used for correcting the information signal to achieve a certain value when the gas sensor element is operated, and
   wherein the compensating resistor is electrically and parallelly connected to the paired electrodes of the oxygen generating cell through a current flow line other than a current flow line that has at least one of the solid electrolyte substrates as an essential part of the current flow line.

2. A gas sensor element as claimed in claim 1, in which the compensating resistor is covered with a protecting layer to protect the compensating resistor from surrounding gas, the protecting layer being provided on an outer surface of the gas sensor element.

3. A gas sensor element as claimed in claim 1, in which the compensating resistor is trimmed to have an adjustable resistance value that is reflected by the correction information.

4. A gas sensor comprising:
a gas sensor element as claimed in claim 1; and
a housing that holds therein the gas sensor element.

5. A gas sensor control system comprising:
a gas sensor as claimed in claim 4; and
a control unit electrically connected to the gas sensor and provided in a place apart from the gas sensor, wherein the control unit comprises:
a first processor that provides a first information signal representative of the resistance value of the compensating resistor;
a second processor that provides a second information signal representative of the concentration of the oxygen; and
a third processor that calculates the correction information in accordance with the first information signal and corrects the second information signal in accordance with the calculated correction information.

6. A gas sensor for detecting a concentration of oxygen in a gaseous environment and outputting an information signal representative of the concentration of the oxygen, the gas sensor comprising:
a gas sensor element and a housing that holds therein the gas sensor element, wherein the gas sensor element comprises an elongated plate-shaped detecting element which extends in a lengthwise direction of the gas sensor element, and includes a lower side and an upper side opposing one another, as seen in a thickness direction perpendicular to the lengthwise direction, and an elongated plate-shaped heater which extends in the lengthwise direction and is laminated on a surface of the lower side of the elongated plate-shaped detecting element,
the elongated plate-shaped detecting element including:
an insulating substrate disposed on the upper side,
an integrated compensating resistor which is provided on an upper surface of the insulating substrate distally to the elongated plate-shaped heater, and
at least one pump cell and an oxygen generating cell arranged on a side of the insulating substrate opposite the compensating resistor, each of the at least one pump cell and the oxygen generating cell including a solid electrolyte substrate and a pair of electrodes having the solid electrolyte substrate put therebetween,
wherein the oxygen generating cell generates the oxygen when a constant current is forced to flow through the paired electrodes of the oxygen generating cell,
wherein the compensating resistor compensates for a variation in an oxygen concentration detecting result of the gas sensor element, and has a resistance value determined in advance according to the oxygen concentration detecting characteristic of the gas senor element which is lower than a resistance value of the solid electrolyte substrate under condition of room temperature and is more than ten times as much as a resistance value of the solid electrolyte substrate under a condition of 800° C.,
wherein the resistance value of the compensating resistor reflects correction information used for correcting the information signal to achieve a certain value when the gas sensor element is operated, and
wherein the compensating resistor is electrically and parallelly connected to the paired electrodes of the oxygen generating cell through a current flow line other than a current flow line that has at least one of the solid electrolyte substrates as an essential part of the current flow line.

7. A gas sensor element as claimed in claim 1, wherein the compensating resistor is electrically connected to the pair of electrodes of the oxygen generating cell by first and second electrically conductive through holes extending through the insulating substrate.

8. The gas sensor element as claimed in claim 1, wherein a relationship between the correction information and resistance values is stored in a table,
the compensating resistor is connected in parallel to a resistance value reading circuit configured to read out the resistance value of the compensating resistor,
the resistance value of the compensating resistor is matched to the correction information by referencing the table, and
the information signal is corrected based on the matched correction information.

* * * * *